United States Patent
Schadewaldt et al.

(10) Patent No.: US 10,114,098 B2
(45) Date of Patent: Oct. 30, 2018

(54) METHOD ESTIMATING A PSEUDO HOUNSFIELD UNIT VALUE

(71) Applicant: KONINKLIJKE PHILIPS N.V., Eindhoven (NL)

(72) Inventors: Nicole Schadewaldt, Eindhoven (NL); Michael Gunter Helle, Eindhoven (NL); Heinrich Schulz, Eindhvoen (NL); Steffen Renisch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 3 days.

(21) Appl. No.: 15/300,052

(22) PCT Filed: Mar. 17, 2015

(86) PCT No.: PCT/EP2015/055539
§ 371 (c)(1),
(2) Date: Sep. 28, 2016

(87) PCT Pub. No.: WO2015/150065
PCT Pub. Date: Oct. 8, 2015

(65) Prior Publication Data
US 2017/0131375 A1 May 11, 2017

(30) Foreign Application Priority Data
Apr. 1, 2014 (EP) .................................... 14163038

(51) Int. Cl.
*G01R 33/56* (2006.01)
*G06T 7/00* (2017.01)
(Continued)

(52) U.S. Cl.
CPC ........ *G01R 33/5608* (2013.01); *A61B 5/0042* (2013.01); *A61B 5/055* (2013.01);
(Continued)

(58) Field of Classification Search
CPC ... G01R 33/5608; A61B 5/0042; A61B 5/055; G06T 7/11; G06T 7/0012; G06T 2207/10088
See application file for complete search history.

(56) References Cited

U.S. PATENT DOCUMENTS

| | | | |
|---|---|---|---|
| 6,466,687 B1 * | 10/2002 | Uppaluri | G06T 7/0012 382/128 |
| 2002/0186875 A1 * | 12/2002 | Burmer | G06K 9/00127 382/133 |

(Continued)

FOREIGN PATENT DOCUMENTS

WO 2013144799 A1 10/2013

OTHER PUBLICATIONS

Stehning et al "MR Based Attenuation Mapping of the Pelvis Using 3D UTE Dixon at 3T" International Society for Magnetic Resonance in Medicine 21 (2013) p. 2811.
(Continued)

*Primary Examiner* — Qian Yang (57) ABSTRACT

A pseudo CT Hounsfield Unit value for a volume element within a subject is estimated from a plurality of magnetic resonance images having different contrasts. The method includes determining a relative prevalence of a first tissue class and second tissue class within the volume element from a first magnetic resonance image and a second magnetic resonance image, respectively. Then a relative prevalence of a third tissue class is determined within the volume element based on substraction of a relative prevalence of the first and/or second tissue class from a total tissue prevalence. A reference Hounsfield Unit value is provided for the first, second and third tissue class. Finally, a pseudo Housfield value is estimated for the volume element by determining a weighted sum of the first, second and third reference Hounsfield unit value, with weight factors which are based on the determined relative prevalences of the first, second and third tissue class.

12 Claims, 4 Drawing Sheets

(51) Int. Cl.
  *G06T 7/11* (2017.01)
  *G01R 33/48* (2006.01)
  *A61B 5/055* (2006.01)
  *A61B 5/00* (2006.01)

(52) U.S. Cl.
  CPC ....... *G01R 33/481* (2013.01); *G01R 33/4828* (2013.01); *G06T 7/0012* (2013.01); *G06T 7/11* (2017.01); *G06T 2207/10088* (2013.01); *G06T 2207/30008* (2013.01); *G06T 2207/30024* (2013.01)

(56) References Cited

U.S. PATENT DOCUMENTS

| | | | | |
|---|---|---|---|---|
| 2010/0021034 | A1* | 1/2010 | Lenglet | G06K 9/342 382/131 |
| 2012/0263361 | A1* | 10/2012 | Boettger | G06T 7/0081 382/131 |
| 2013/0039558 | A1 | 2/2013 | Balter et al. | |
| 2014/0133728 | A1* | 5/2014 | Blaffert | G06T 7/0012 382/131 |
| 2016/0310761 | A1* | 10/2016 | Li | A61N 5/1038 |

OTHER PUBLICATIONS

Christian Buerger, Jochen Peters, et al., 'Multi-modal vertebra segmentation from MR Dixon for hybrid whole-body PET/MR', In: J. Yao, T. Klinder and S. Li editors. Proceeding of MICCAI 2013 Workshop on Computational Methods and Clinical Applications for Spine Imaging. 2013; pp. 144-155.

Marloes Frantzen-Steneker, Michael Helle, et al., In-vivo dosimetric evaluation of an atlas based labeling technique using MR DIXON for MR-only RT treatment planning, abstract accepted at ESTRO 2014.

Adam Johnsson, Mikael Karlsson and Tufve Nyholm, CT substitute derived from MRI sequences with ultrashort echo time. In Medical Physics 38 (5) May 2011.

Michael Helle, Nicole Schadewaldt, et al. 'Evaluation of Dixon based Soft Tissue and Bone Classification in the pelvis for MR only based Radiation Therapy Planning', abstract accepted at ISMRM 2014.

Kawaguchi Hiroshi et al: "A proposal for PET/MRI attenuation correction with[mu]-values measured using a fixed-position radiation source and MRI segmentation",Nuclear Instruments & Methods in Physics Research. Section A: Accelerators, Spectrometers, Detectors, and Associated Equipment, vol. 734, Sep. 6, 2013 (Sep. 6, 2013),pp. 156-161.

Johansson Adam et al: "CT substitute derived from MRI sequences with ultrashort echo time", Medical Physics, AIP, Melville, NY, US, vol. 38, No. 5, May 9, 2011 (May 9, 2011), pp. 2708-2714.

"Handbook of MRI Pulse Sequences" Bernstein et. al., published by Elsevier Academic Press (2004) p. 857-887.

* cited by examiner

METHOD ESTIMATING A PSEUDO HOUNSFIELD UNIT VALUE

CROSS REFERNCE TO RELATED APPLICATIONS

This application is a U.S. national phase application of International Application No. PCT/EP2015/055539, filed on Mar. 17, 2015, which claims the benefit of EP Application Ser. No. 14163038.4 filed on Apr. 1, 2014 and is incorporated herein by reference.

FIELD OF THE INVENTION

The invention relates to magnetic resonace imaging, in particular to the creation of pseudo pseudo Housfield value for voxels.

BACKGROUND OF THE INVENTION

Creating estimated electron density maps from magnetic resonance (MR) images is a problem that occurs e.g. with integrated PET/MR systems, where an attenuation maps needs to be estimated, or with radiation therapy planning based on MR, where electron density maps are required for the treatment simulation. However, due to the physics of the image acquisition, MR intensities do not uniquely correspond to electron density, hence those maps cannot be derived from the MR image by a simple lookup operation, as is commonly done when estimating these maps from CT images.

For radiotherapy planning, attenuation coefficients are required for dose calculation. Today, these coefficients are derived from CT images' HU values. However, increasingly often MR-images are acquired for diagnostic purpose or organ delineation prior to treatment planning Dose calculation based on only MR images would be highly beneficial in those cases, as this would eliminate the need for additional CT images for dose calculation and thus simplify the workflow and reduce radiation dose. For the development of MR-Linac systems with online treatment planning, an MR based dose calculation will be essential.

There are approaches known from the literature addressing the problem of estimating pseudo CT HU values from MR images. It is an insight of the invention that those still suffer from shortcomings. Specific problems with the different approaches are explained below.

For instance, registration of a CT based density atlas to the MR image may help in regions, where the atlas values are confined and reliable, e.g. the brain. However, in highly variable anatomical regions like the pelvic region, registration may not be able to cover the anatomical variations between patients, e.g. bladder/bowel filling or movement, resection of structures (e.g. kidneys, liver parts) or pathologic changes.

Other approaches divide the MR image into a number of tissue classes, e.g. bone, tissue and air, and assign average CT values to each tissue classes to simulate a CT image. The resulting image represents the patient anatomy at the tissue boundaries, however, the bulk values per tissue class ignore fine differences and structure within the tissue. Especially in bone tissue, CT intensities vary highly between cortical bone, trabecular structure and marrow parts. Further, partial volume effects are ignored, which is especially problematic for thin structures, e.g. the cortical bone.

A third class of approaches models a joint intensity distribution between CT numbers and a set of MR images and features derived from the MR images. The underlying assumption is that each tissue class has specific values in each of the MR images and can be modeled by a multi-dimensional Gaussian intensity value distribution. A multi-variate Gaussian mixture model for the joint distribution of intensities is trained from images of different patients and then applied to the MR images and image-derivates of a new patient. To account for tissue-mixtures and for partial volume effects, e.g. tissue or voxels containing both bone and fat, more Gaussians than expected anatomical tissue types are used for the model. However, this is a definite drawback of the method, since only tissue-mixture types represented by a separate Gaussian can be assigned reliably. Further, to train the joint intensity distribution model a good correspondence between registered CT positions and MR positions is necessary. This may be achievable in the head, where there is little anatomical variation between acquisitions, however, for highly variable regions, such as the pelvis, this strong correlation of intensity values for training may not be achievable.

A common approach is to prescribe an average HU value to tissues derived from the MR image. Another common approach is to interpolate between different MR imaging contrasts.

WO2013144799A1 describes a magnetic resonance system that generates an attenuation or density map. The system includes a MR scanner defining an examination volume and at least one processor. The at least one processor is programmed to control the MR scanner to apply imaging sequences to the examination volume. In response to the imaging sequences, MR data sets of the examination volume are received and analyzed to identify different tissue and/or material types found in pixels or voxels of the attenuation or density map. One or more tissue-specific and/or material-specific attenuation or density values are assigned to each pixel or voxel of the attenuation or density map based on the tissue and/or material type(s) identified as being in each pixel or voxel during the analysis of the MR data sets.

The journal article Kawaguchi et. al., "A proposal for PET/MRI attenuation correction with µ-values measured using a fixed-position radiation source and MRI segmentation." Nuclear Instruments and Methods in Physics Research Section A: Accelerators, Spectrometers, Detectors and Associated Equipment 734 (2014): 156-161. doi:10.1016/j.nima.2013.09.015 discloses a method of determing individual µ-values for the brain. The µ-values are determined by placing a radiation source in a fixed position within a PET/MRI scanner. A MRI image of a subject is segmented into tissues posseing homogeneous µ-values and the radiation attenuation by the subject is measured. The measured radiation attenuation is then used to assigne the µ-values to the homogeneous regions.

SUMMARY OF THE INVENTION

The invention provides for a method, a magnetic resonance imaging system, and a computer program product in the independnet claims. Embodiments are given in the dependnet claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit,"

"module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A Magnetic Resonance Imaging (MRI) image or Magnetic Resonance Image is defined herein as being the reconstructed two or three dimensional visualization of anatomic data contained within magnetic resonance imaging data. This visualization can be performed using a computer. Magnetic Resonance (MR) data is defined herein as being the recorded measurements of radio frequency signals emitted by atomic spins using the antenna of a Magnetic resonance apparatus during a magnetic resonance imaging scan.

It is an object of the invention to improve the estimation of pseudo CT Hounsfield Unit (HU) values from magnetic resonance images.

In one aspect, the invention provides for a method for estimating a pseudo CT Hounsfield Unit value for a volume element within a subject from a plurality of magnetic resonance images having different contrasts, the method comprising the steps of:
  determination of a relative prevalence of a first tissue class within the volume element from the plurality of magnetic resonance images;
  determination of a relative prevalence of a second tissue class within the volume element from the plurality of magnetic resonance images;
  determination of a relative prevalence of a third tissue class within the volume element based on substraction of a relative prevalence of the first and/or second tissue class from a total tissue prevalence;
  providing a first reference Hounsfield unit value for the first tissue class
  providing a second reference Hounsfield unit value for the second tissue class
  providing a third reference Hounsfield unit value for the third tissue class
  estimating a pseudo Housfield value for the volume element by determining a weighted sum of the first, second and third reference Hounsfield unit value, with weight factors which are based on the determined relative prevalences of the first, second and third tissue class.

In one example, the third tissue class is bone or air.

This embodiment may have the advantage that the estimation of pseudo CT Hounsfield Unit (HU) values from magnetic resonance images.

By determinination of a weighted contribution of different tissue classes pseudo HU values for different tissue classes can be easily combined. Signal intensities inside a volume element for different tissue classes (retrieved from different MR images) can simply be compared with each other to determine the tissue classes' individual contributions to the pseudo HU value.

Using MR imaging it is complicated to directly determine a pseudo Hounsfield value for certain types of tissue classes as some tissue classes do not show signal on an MR image. By substracting relative prevalence of a first and/or second tissue class from a total tissue prevalence also a relative prevalence for low signal tissue classes can be obtained. In turn this information can be used to calculate a pseudo Hounsfield unit value for a volume element comprising a low signal tissue class. Thereby, the proposed method improves the estimation of pseudo CT Hounsfield Unit (HU) values from magnetic resonance images.

According to embodiments of the invention tissue, that is not water or fat, is assumed to be the third tissue class. The third tissue class is assumed to be bone within a bone-segmentation and air outside the bone-segmentation. This embodiment may be advantageous, because it can help to distinguish between bone and air, which both show no signal on MR, but show different CT HU values. As image segmentation by itself is well-known in the art, image segmentation will not be described in more detail.

Alternatively, every bone can be considered individually, as typical HU values for bone depend on the bone density. E.g. the cortical part of a femur bone is much more dense than cortical part of the sacrum. This opens up a whole suite of third tissue classes such as for example air, femur, pelvis, sacrum, coggyx, vertebrae.

Furthermore, "air" could be further differentiated as "Outside Air" and "Bowel Air", as they can be treated differently in radiotherapy planning E.g. Bowel-Air may be given a density similar to water. This could be more adequate for treatment planning, as the bowel air is likely going to move during treatment. Consequently, air may also refer to a suite of tissue classes.

Other examples of the third tissue class could be metal-containing structures, e.g. seeds or implants.

It is especially advantageous to determine relative prevalences of different tissue classes from MR images which artifacts and thereby signal intensities are related, e.g. because the images were acquired within a single sequence or with a similar sequence. Hereby, artifacts in the images may cancel each other when generating pseudo CT HU values by means of weighted contributions. Also for these types of images exact quantification becomes less important. An example of such images are DIXON fat and DIXON water images. According to one embodiment DIXON fat and water images are used as an input for the method according to the invention. The advantage of DIXON water and fat images is that they show both (mainly) signal arising from water and signal arising from fat, where mostly one signal is clearly stronger than the other, such that the image can be divided into a 'mainly fat' and a 'mainly water' image. Therefore, these images are useful to determine a relative prevalence, which is then clearly superior to the mutually exclusive 'water/fat' distinction done in prior art publications. As discussed above another advantage of a DIXON technique is that images comprising information on different tissue classes are related to each other such that potential artifacts contribute in a similar way to all images. As a result the contribution of artifacts to the pseudo Hounsfield unit values is small and exact quantification of the MR signal is of less importance. As DIXON techniques are well-known in the art of MR imaging, this technique will not be described in further detail.

The terminology to describe the Dixon technique is well known and has been the subject of many review articles and is present in standard texts on Magnetic Resonance Imaging. For example "Handbook of MRI Pulse Sequences" by Bernstein et. al., published by Elsevier Academic Press in 2004 contains a review of some Dixon techniques on pages 857 to 887.

According to an embodiment of the invention a signal intensity for a tissue class is scaled using a threshold for the signal of the tissue class. This could for example be done such that above this threshold the signal is considered 'maximal=1', where below the absolute signal intensity is rescaled between 0 and 1. This scaling is especially advantageous if next to this first (and/or second) tissue class within a region also the relative prevalence of a third tissue class needs to be determined which third tissue class shows limited or no signal on MR images.

Further, according to embodiments of the invention, to incorporate differences between signal strength of different tissues, a weighting factor may be used to compute the relative prevalence.

All these embodiments could be implemented in a computer program product, which computer program product comprises executable code to perform method steps of the invention. Such computer program product could be a stand-alone product, but could also be combined with other computer program product or be part of a magnetic resonance system.

These and other aspects of the invention will be apparent from and elucidated with reference to the embodiments described hereinafter.

It is understood that one or more of the aforementioned embodiments of the invention may be combined as long as the combined embodiments are not mutually exclusive.

BRIEF DESCRIPTION OF THE FIGURES

In the following preferred embodiments of the invention will be described, by way of example only, and with reference to the drawings in which.

DETAILED DESCRIPTION OF THE INVENTION

Like numbered elements in these figures are either equivalent elements or perform the same function. Elements which have been discussed previously will not necessarily be discussed in later figures if the function is equivalent.

Figure 1:
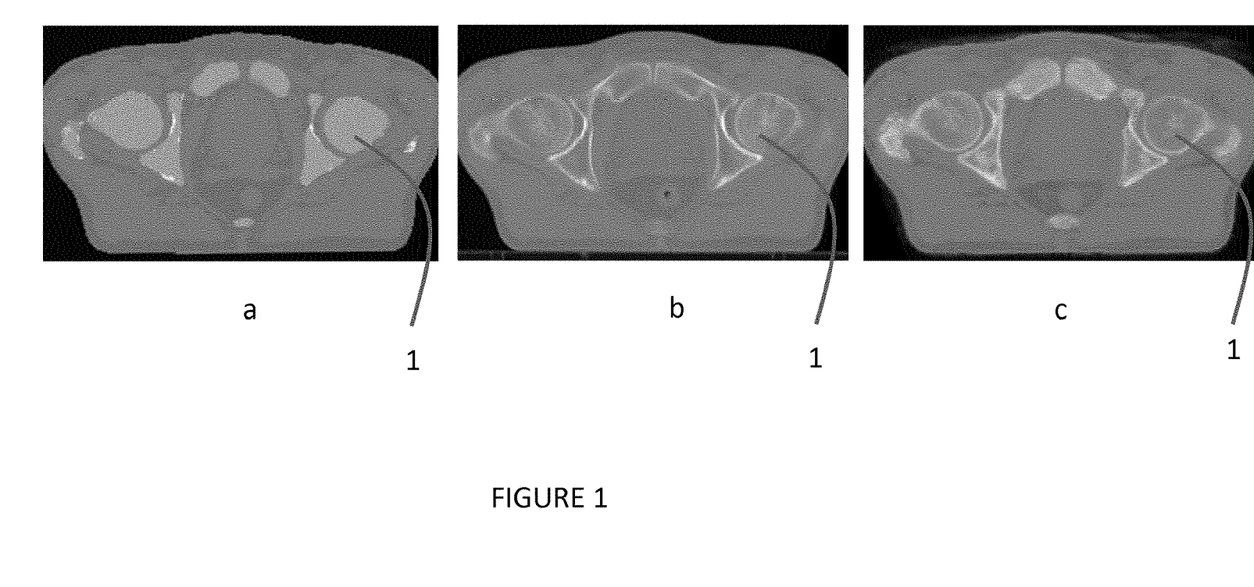
FIG. 1 shows a comparison between a pseudo CT according to the prior art (a), a true CT (b) and a pseudo CT image according to an embodiment of the invention (c).

FIG. 1 shows a comparison between a pseudo CT image according to the prior art (a), a true CT image (b) and a pseudo CT image derived according to an embodiment of the invention (c). FIG. 1a is generated by average HU value assignment to water and fat (Dixon-reconstruction), air (body outline detection) and cortical and cancellous bone (segmentation+threshold). FIG. 1c is generated by interpolation of average CT values based on relative prevalence as proposed using bone segmentation. For the generation of FIG. 1c no body-outline detection was used. FIG. 1c shows a lot more detail in bone tisse 1 compared to FIG. 1a. Furthermore, FIG. 1c is visually more similar to FIG. 1b then FIG. 1a.

Figure 2:
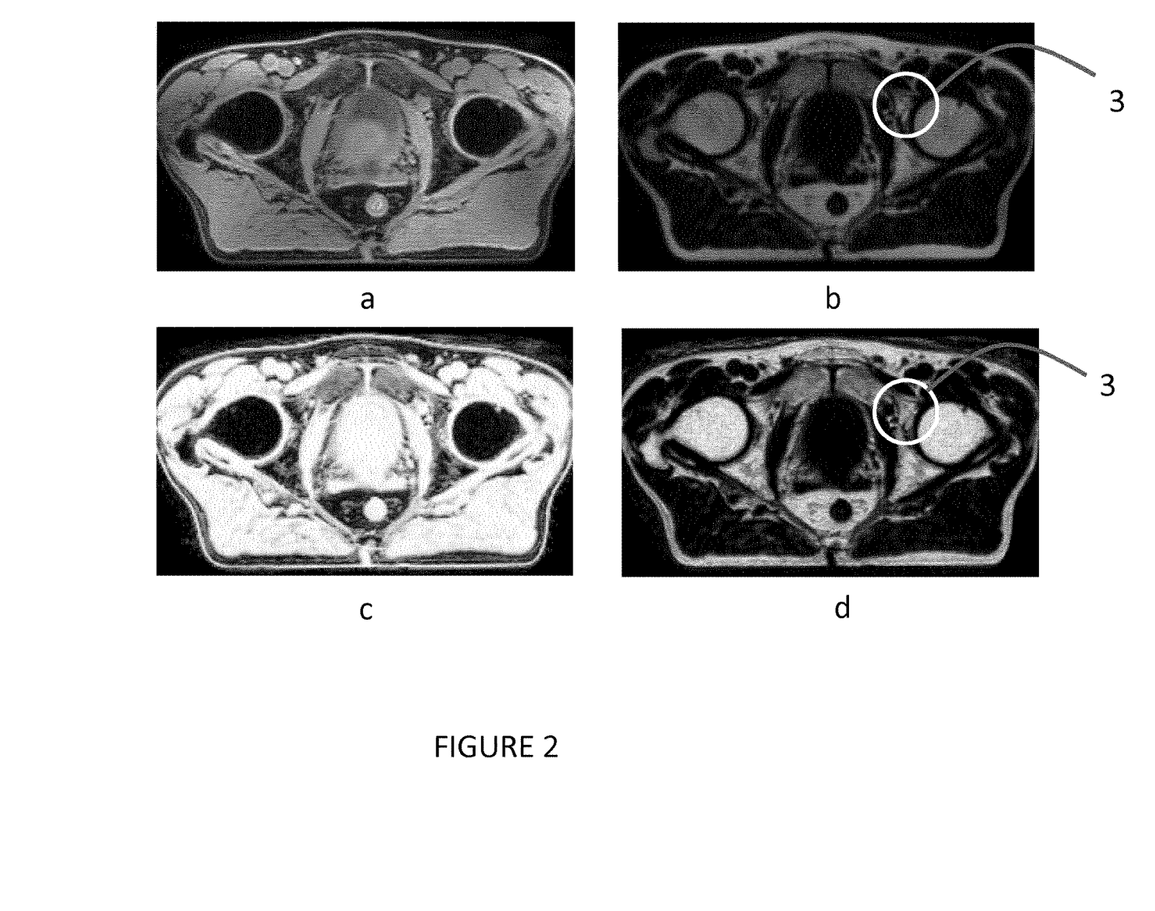
FIG. 2 shows intensity values in Dixon reconstructed images (a,b) and in computed relative prevalences (c,d).

FIG. 2 shows intensity values in Dixon reconstructed images (a,b) and in computed relative prevalences (c,d). The relative prevalence images (c,d) appear mainly brighter, however, within circle 3 one can see, that the absolute intensity in two regions (femur head and hip joint) may be the same in the fat image, but be weighted differently in the relative prevalence image—this is due to the different contribution of water signal in these voxels.

Given a plurality of MR images, signal can be attributed to a number of different tissue classes. According to one embodiment, water and fat signal is distinguished via a DIXON reconstruction. The relative prevalence of water can be computed as follows:

$$p_{water} = \min\left\{1, \frac{s_{water}}{threshold_{water}}\right\} \cdot \frac{s_{water}}{s_{water} + s_{fat} + \epsilon}$$

Here, $s_{water}$ is the intensity in the Dixon-reconstructed water image, and $threshold_{water}$ is a tissue specific threshold to re-scale water intensities between 0 and threshold. If $s_{fat}=0$ and $\epsilon$ is neglected, then for $s_{water}<threshold_{water}$ the relative prevalence of water, $p_{water}$, is a linear function of $s_{water}$, which is 0 if $s_{water}=0$ and 1 if $s_{water}\geq threshold_{water}$. For more than two tissues, the relative prevalence is computed as:

$$p_{tissue} = \min\left\{1, \frac{s_{tissue}}{threshold_{tissue}}\right\} \cdot \frac{s_{tissue}}{\sum_i s_{tissue_i} + \epsilon}$$

Figure 3:
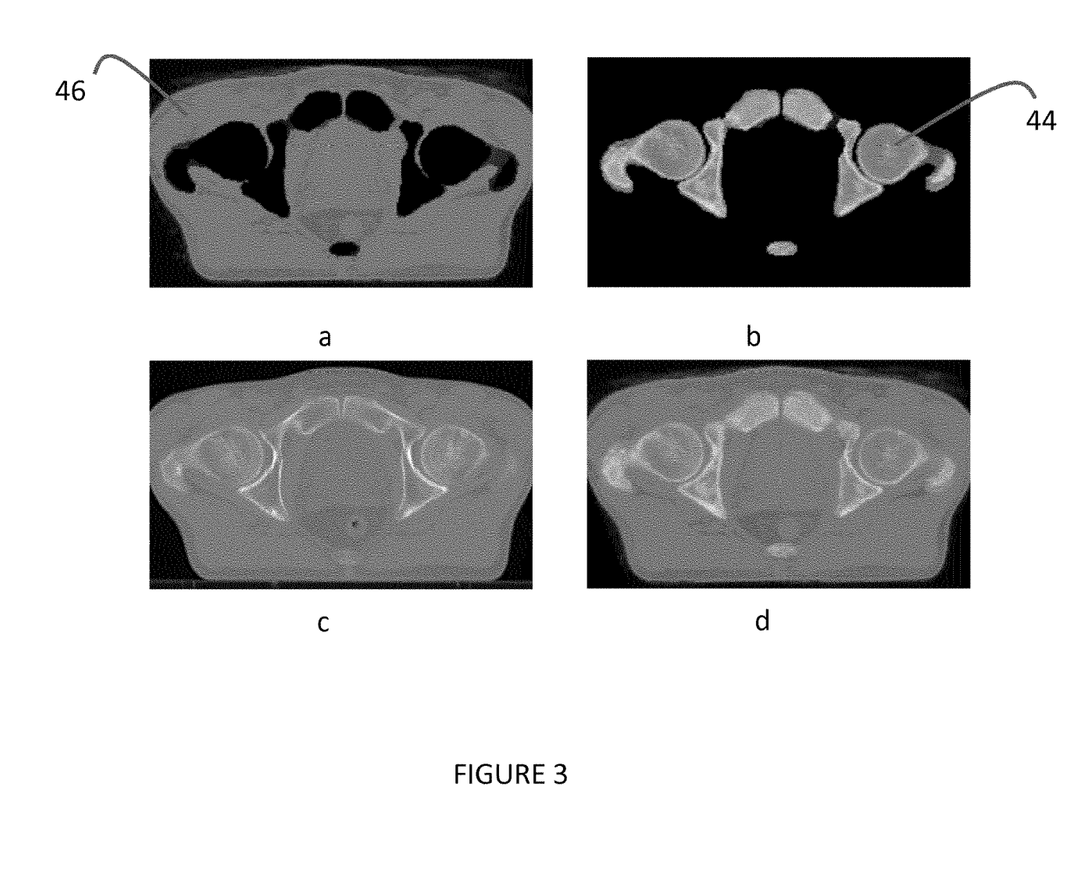
FIG. 3 shows an example of how a relative prevalence can be determined for a tissue class not providing a signal on the MR images.

The factors on the right sum up to 1. The underlying assumption for using the first factor is, that there may be a tissue contained in the voxel which does give practically no signal. FIG. 3 shows an example of how a relative prevalence can be determined for a tissue class not providing a signal on the MR images. For example, bone and air tissue do not exhibit signal on a T1-Dixon MR sequence. Since $p_{tissue} \in [0, 1]$, we can also define a tissue fraction for the non-signal tissue, i.e.:

$$P_{non-signal-tissue} = 1 - \sum_i p_{tissue_i}$$

According to embodiments of the invention, a region containing bone tissue is distinguished via a model based segmentation based on both water and fat images. An example of such a bone segmented region can be seen in FIG. 3b, 44. Then the HU value for a simulated CT image can be interpolated from average (reference) HU values of each of the relevant tissue types: water, fat and either bone within the bone segmentation or air outside the bone segmentation:

$$HU_{simCT-BONE}=(1-p_{water}-p_{fat})\cdot HU_{bone}+ p_{water}\cdot HU_{water}+p_{fat}\cdot HU_{fat}$$

$$HU_{simCT-AIR}=(1-p_{water}-p_{fat})\cdot HU_{air}+p_{water}\cdot HU_{water}+ p_{fat}\cdot HU_{fat}$$

FIG. 3a shows an example of a region 46 outside the bone region 44. By combining FIGS. 3a and 3b, a pseudo CT HU image can be retrieved, FIG. 3d. As a comparison a true CT image is shown in FIG. 3c.

The HU-value interpolation based on relative prevalence may be used with or without the consideration of a signal-free tissue like bone and air. If it is used without a signal-free tissue, the first factor should preferably be omitted, otherwise the interpolation is identical to assuming a signal-free tissue with average intensity 0. Parameters like the tissue specific threshold may be based on experience or trained from known MR/CT value correspondences. Further, to incorporate differences between signal strength of different tissues, a weighting factor may be used to compute the relative prevalence (here 'tissue' corresponds to a single one of 'tissue_i'):

$$p_{tissue} = \max\left\{1, \frac{s_{tissue}}{threshold_{tissue}}\right\} \cdot \frac{w_{tissue}\cdot s_{tissue}}{\sum_i w_{tissue_i}\cdot s_{tissue_i} + \epsilon}$$

Resulting interpolated HU values are based on the voxel-wise true MR signal from the patient and very little parameters need tuning or training.

The essential component of this invention is the principle to deduce a relation of certain tissues (voxelwise) from the Patient specific MR images and base a reference value interpolation for simulating CT images on this relative prevalence. The above used MR-T1-Dixon sequence and the formulas are just one possible way of implementing the estimation of relative prevalence. However, the invention itself is not restricted to these MR images or these specific formulas.

Figure 4:
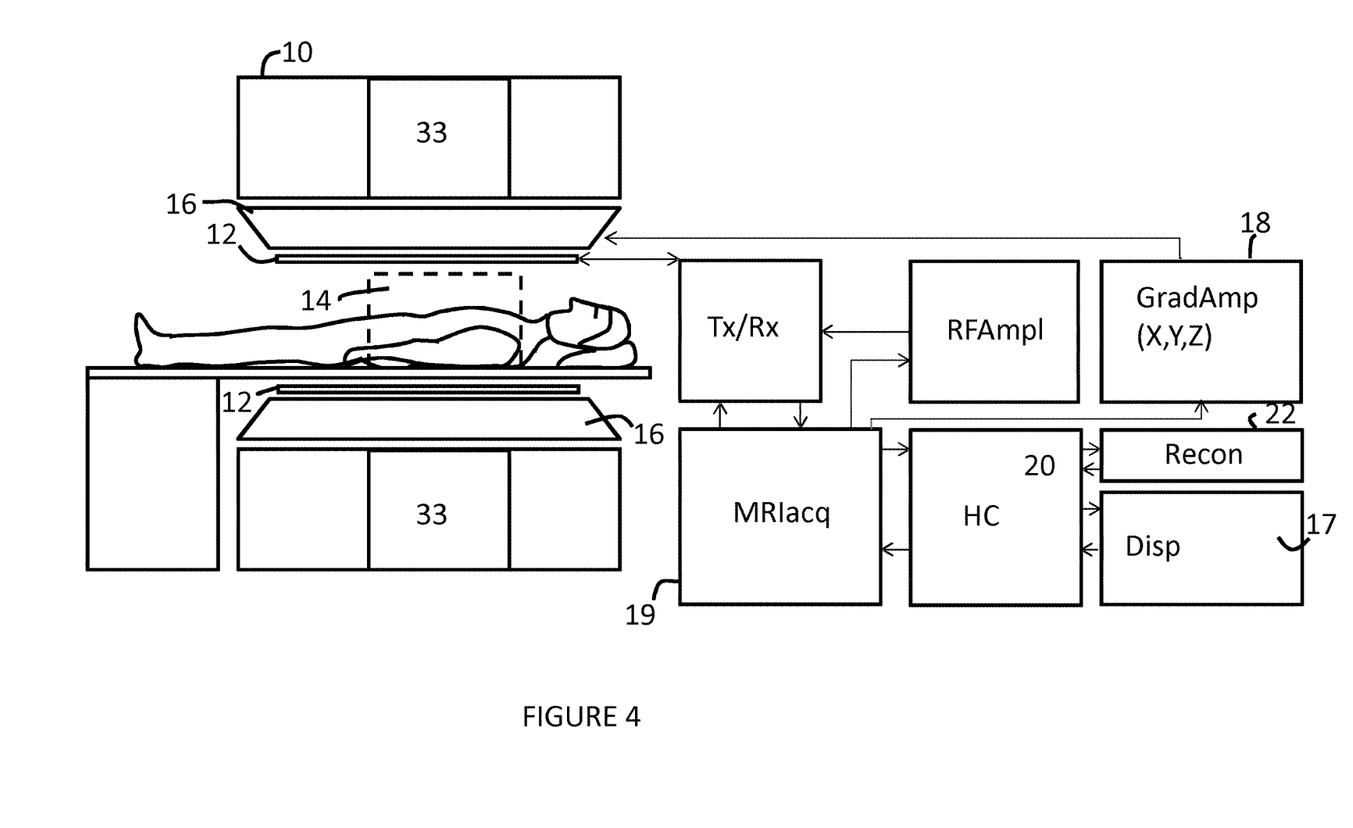
FIG. 4 shows an embodiment of the MR system according to the invention.

FIG. 4 shows an embodiment of the MR system according to the invention. The MR system comprises a main magnet 10 which generates a steady homogeneous main magnetic field within the examination zone 14. This main magnetic field causes a partial orientation of the spins in the object to be examined along the field lines of the main magnetic field. An RF system is provided with one or more RF antennae 12 to emit an RF excitation electromagnetic field into the examination zone 14 to excite spins in the body of the object to be examined. The relaxing spins emit magnetic resonance signals in the RF range which are picked up by the RF antennae 12, notably in the form of RF receiving coils. Further, gradient coils 16 are provided to generate temporary magnetic gradient fields, notably read gradient pulses and phase encoding gradients. These gradient fields usually are orientated in mutual orthogonal directions and impose spatial encoding on the magnetic resonance signals. Gradient amplifiers 18 are provided to activate the gradient coils 16 to generate the magnetic gradient encoding fields. The magnetic resonance signals picked up by the RF receiver antennae 12 are applied to an MRI data acquisition system 19 which includes a spectrometer. The MRI data acquisition system provides the data to a host computer 20, which in turn provides it to a reconstructor 22, which reconstructs an image from the data. The reconstructed image can be displayed on display 17. The host computer could comprise a computer program product comprising program code means for performing the steps of an embodiment.

The computer program product could also be a stand-alone program, which could for example be executed from a standard computer/workstation. Also the computer program product could be made available e.g. as a plugin to standard radiotherapy planning software or attenuation correction software or to upgrade the MR system.

The MR system could further comprise a radiotherapy system 33 for performing a radiotherapy treatment dependent on the estimated pseudo Hounsfield unit value or a PET scanner 33 configured to determine an attenuation correction based the estimated pseudo Hounsfield unit value.

Whilst the invention has been illustrated and described in detail in the drawings and foregoing description, such illustrations and description are to be considered illustrative or exemplary and not restrictive; the invention is not limited to the disclosed embodiments and can be used for generation of pseudo CT images from magnetic resonance images.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program or computer program product may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method comprising, with one or more processors, performing the steps of:
    determining a relative prevalence of a first tissue class within each of a plurality of volume elements in a region of a subject from a plurality of magnetic resonance images having different contrasts;
    determining a relative prevalence of a second tissue class within each of the volume elements in the region of the subject from the plurality of magnetic resonance images;
    determining a relative prevalence of a third tissue class within each of the volume elements in the region of the subject based on subtraction of a relative prevalence of the first and/or second tissue class from a total tissue prevalence within each of the volume elements;
    providing a first reference Hounsfield unit value for the first tissue class;
    providing a second reference Hounsfield unit value for the second tissue class;
    providing a third reference Hounsfield unit value for the third tissue class;
    estimating a pseudo CT Hounsfield unit value for each of the plurality of volume elements within the region of the subject by determining a weighted sum of the first, second, and third reference Hounsfield unit values with weighting factors based on the determined relative prevalences of the first, second, and third tissue classes to form a pseudo CT Hounsfield unit image representation of the region of the subject; and
    at least one of:
        providing positron emission tomography (PET) imaging data from the region of the subject, and with the pseudo CT Hounsfield unit image representation, attenuation correcting the PET imaging data and reconstructing the attenuation corrected PET imaging data into an attenuation corrected PET image, and displaying the attenuation corrected PET image on a display device, and
        from the pseudo CT Hounsfield unit image and at least one of the plurality of magnetic resonance images, generating a radiation therapy plan, and controlling a radiation therapy device to irradiate the region of the subject in accordance with the radiation therapy plan.

2. The method as claimed in claim 1, wherein the first tissue class is water and the second tissue class is fat.

3. The method as claimed in claim 2, wherein the plurality of magnetic resonance images comprise a DIXON water image and a DIXON fat image.

4. The method as claimed in claim 1, wherein a signal intensity for a tissue class is scaled by a threshold for the signal of the tissue class.

5. The method as claimed in claim 1, wherein the plurality of volume elements are disposed in an array forming the pseudo CT Hounsfield image and further comprising:
    segmenting the volume elements of the third tissue class and determining the CT Hounsfield Unit value for the third tissue class from the segmented volume elements.

6. The method as claimed in claim 1, wherein the third tissue class is bone or air.

7. The method as claimed in claim 1, further including computing one or more weighting factors for computing the relative tissue prevalence.

8. The method as claimed in claim 1, further including:
    combining the attenuation corrected PET image and at least one of the magnetic resonance images to generate a hybrid PET/MR image; and
    displaying the hybrid PET/MR image on the imaging device.

9. A magnetic resonance system comprising one or more processors configured to:
    acquire a plurality of magnetic resonance images having different contrasts for a region of a subject;
    determine a relative prevalence of a first tissue class within each of the plurality of volume elements in the region of the subject from the plurality of magnetic resonance images;
    determine a relative prevalence of a second tissue class within each of the plurality of volume elements in the region of the subject from the plurality of magnetic resonance images;
    determine a relative prevalence of a third tissue class within each of the plurality of volume elements in the region of the subject based on subtraction of a relative prevalence of the first and/or second tissue class from a total tissue prevalence within each of the plurality of volume elements;
    provide a first reference Hounsfield unit value for the first tissue class;
    provide a second reference Hounsfield unit value for the second tissue class;
    provide a third reference Hounsfield unit value for the third tissue class;
    estimate a pseudo CT Hounsfield unit value for each of the plurality of volume elements within the region of the subject by determining a weighted sum of the first, second, and third reference Hounsfield unit values with weighting factors based on the determined prevalences of the first, second, and third tissue classes to form a pseudo CT Hounsfield unit image representation of the region of the subject; and at least one of:
provide positron emission tomography (PET) imaging data from the region of the subject, and with the pseudo CT Hounsfield unit image representation, attenuation correct the PET imaging data and reconstruct the attenuation corrected PET imaging data into an attenuation corrected PET image, and displaying the attenuation corrected PET image on a display device, and from the pseudo CT Hounsfield unit image and at least one of the plurality of magnetic resonance images, generate a radiation therapy plan, and control a radiation therapy device to irradiate the region of the subject in accordance with the radiation therapy plan.

10. A system comprising:
a radiotherapy system configured to perform a radiotherapy treatment on a volume region of a subject based on a radiation therapy plan;
a magnetic resonance imager including a main magnet configured to partially orient spins in the volume regions of the subject, one or more RF antenna configured to emit an RF excitation field into the volume regions of the subject to excite spins and pick up relaxing spins as magnetic resonance signals, gradient coils and gradient amplifiers configured to generate temporary magnetic gradient fields to impose spatial encoding on the magnetic resonance signals;
one or more processors configured to:
reconstruct the spatially encoded magnetic resonance signals into magnetic resonance images of the volume region of the subject,
determine a relative prevalence of a first tissue class within each volume element of an array of volume elements from the plurality of magnetic resonance images,
determine a relative prevalence of a second tissue class within each volume element of an array of volume elements from the plurality of magnetic resonance images,
determine relative prevalence of a third tissue class within each volume element of the array of volume elements based on subtraction of a relative prevalence of the first and/or second tissue class from a total tissue prevalence,
receive a first reference Hounsfield unit value for the first tissue class,
receive a second reference Hounsfield unit value for the second tissue class,
receive a third reference Hounsfield unit value for the third tissue class,
estimate a pseudo CT Hounsfield unit value for each volume element by determining a weighted sum of the first, second and third reference Hounsfield unit values, with weighting factors which are based on the determined relative prevalences of the first, second and third tissue classes,
from the pseudo CT Hounsfield unit values for the array of volume elements, generate the radiation therapy plan, and
control the radiotherapy system to irradiate a volume of regions of the subject in accordance with the generated radiation therapy plan.

11. A non-transitory computer-readable medium carrying program code that, when executed by a processor, causes the processor to perform a method for estimating a pseudo CT Hounsfield Unit value for each of an array of volume elements within a portion of a subject from a plurality of magnetic resonance images having different contrasts, the method comprising the steps of:
determining a relative prevalence of a first tissue class within each of the volume elements from the plurality of magnetic resonance images;
determining a relative prevalence of a second tissue class within each of the volume elements from the plurality of magnetic resonance images;
determining a relative prevalence of a third tissue class within each of the volume elements based on subtraction of a relative prevalence of the first and/or second tissue class from a total tissue prevalence;
providing a first reference Hounsfield unit value for the first tissue class;
providing a second reference Hounsfield unit value for the second tissue class;
providing a third reference Hounsfield unit value for the third tissue class;
estimating the pseudo CT Hounsfield unit value for each of the volume elements by determining a weighted sum of the first, second and third reference Hounsfield unit values, with weight factors which are based on the determined relative prevalences of the first, second and third tissue classes; and
at least one of:
generating a radiation therapy plan from the pseudo CT Hounsfield unit values and controlling a radio therapy system to irradiate the subject based on the radiotherapy plan, and
receiving positron emission tomography (PET) data from a PET scanner, attenuation correcting the PET data based on the pseudo CT Hounsfield unit values, reconstructing the attenuation corrected data to generate an attenuation corrected PET image depicting physical characteristics of the subject, and controlling a display device to display the attenuation corrected PET image.

12. A system comprising:
a positron emission tomography (PET) scanner configured to generate PET data from a volume of the subject containing a plurality of volume elements;
a magnetic resonance imager including a main magnet configured to partially orient spins in the volume regions of the subject, one or more RF antenna configured to emit an RF excitation field into the volume regions of the subject to excite spins and pick up relaxing spins as magnetic resonance signals, gradient coils and gradient amplifiers configured to generate temporary magnetic gradient fields to impose spatial encoding on the magnetic resonance signals;
one or more processors configured to:
reconstruct the spatially encoded magnetic resonance signals into magnetic resonance images of the volume of the subject,
determine a relative prevalence of a first tissue class within each volume element from the plurality of magnetic resonance images,
determine a relative prevalence of a second tissue class within each volume element from the plurality of magnetic resonance images,
determine relative prevalence of a third tissue class within each volume element based on subtraction of a relative prevalence of the first and/or second tissue class from a total tissue prevalence,
receive a first reference Hounsfield unit value for the first tissue class, receive a second reference Hounsfield unit value for the second tissue class, receive a third reference Hounsfield unit value for the third tissue class, estimate a pseudo CT Hounsfield unit value for each of the plurality of volume elements by determining a weighted sum of the first, second and third reference Hounsfield unit values, with weighting factors which are based on the determined relative prevalences of the first, second and third tissue classes, correct the PET data using the pseudo CT Hounsfield unit values and reconstruct the corrected PET data into an attenuation corrected PET image of the portion of the region of the subject.

* * * * *